United States Patent [19]

Davis

[11] 4,235,428
[45] Nov. 25, 1980

[54] BONE TRANSFIXATION PIN GUIDE

[76] Inventor: Jack H. Davis, 650 Sycamore, Glencoe, Ill.

[21] Appl. No.: 20,865

[22] Filed: Mar. 15, 1979

[51] Int. Cl.³ .............................................. B23Q 1/00
[52] U.S. Cl. .................................. 269/53; 269/87.3; 269/203; 128/92 BA
[58] Field of Search ................. 269/87.3, 53, 203; 128/92 BA, 92 BB

[56] References Cited

U.S. PATENT DOCUMENTS

| | | | |
|---|---|---|---|
| 949,096 | 2/1910 | Stetson | 269/53 |
| 2,242,003 | 5/1941 | Lorenzo | 128/92 BB |
| 2,568,233 | 9/1951 | Hamilton | 269/203 |
| 4,137,003 | 1/1979 | Budoff | 269/87.3 |

Primary Examiner—Robert C. Watson
Attorney, Agent, or Firm—Allegretti, Newitt, Witcoff & McAndrews

[57] ABSTRACT

A bone transfixion pin quide includes a body having two spaced, transversely-extending end portions, channel members and prongs for affixing the body in relation to an insertion site. The channel members are on the end portions, and define entrance and exit channels for the bone transfixion pin. In use, the body is affixed in relation to the insertion site, with the entrance and exit channels along the desired path of the bone transfixion pin.

6 Claims, 4 Drawing Figures

BONE TRANSFIXATION PIN GUIDE

BACKGROUND OF THE INVENTION

This invention relates to an orthopedic tool, and more particularly, to a bone transfixion pin guide.

In the practice of orthopedics, the treatment of bone fractures is a prime concern. A common practice in treating fractures is reduction with internal fixation. A method of internal fixation of fractures that is frequently utilized is transfixion by the insertion of a long steel rod through the fragments of the bone, after alignment of the fragments. In the past, such rods, or transfixion pins, have been machined to have tips which can ream bone tissue. The transfixion pins are thus inserted by driving the rod with a power drill or the like so that the tip reams a channel for the pin. Typically, guidance of pin insertion is provided only manually. While this method of insertion of a transfixion pin ultimately results in insertion, there are disadvantages, including the fact that great manual skill is required to insure suitable positioning of the pin.

SUMMARY OF THE INVENTION

In a principal aspect, the present invention is an orthopedic device for guiding the insertion of a pin into an insertion site in a bone so as to transfix the bone. In other words, the present invention is a bone transfixion pin guide.

The bone transfixion pin guide includes a body defining a longitudinal axis and having a first transversely extending end portion and a second transversely extending end portion. The first end portion and the second end portion are spaced longitudinally apart from each other and extend generally in a same transverse direction. The bone transfixion pin guide further includes two channel-defining means and an affixing means. The channel-defining means are a means on the first end portion for defining an entrance channel for the bone transfixion pin and a means on the second end portion for defining an exit channel for the bone transfixion pin. The exit channel is in axial alignment with the entrance channel. The affixing means is means on the first end portion and the second end portion for affixing the body in relation to the insertion site.

With a bone transfixion pin guide as described, a physician can accurately guide the insertion of a bone transfixion pin and accurately select the entrance and exit points into and out of the bone by aligning the entrance and exit channels along the desired path for the bone transfixion pin.

It is thus an object of the present invention to provide an orthopedic tool that improves the method by which bone transfixion pins are inserted into bone fragments.

Another object of the present invention is to provide an orthopedic tool as described, i.e., a bone transfixion pin guide, that guides the insertion of a bone transfixion pin into bone fragments.

Another object of the present invention is to provide a bone transfixion pin guide that is readily adjustable to adapt to the varying physical dimensions of the bones of patients who must be treated for similar fractures.

Another object of the present invention is to provide a bone transfixion pin guide that is readily adjustable to adapt to the varying dimensions of a variety of bone structures.

Another object of the present invention is to provide a bone transfixion pin guide that is capable of retaining itself in a fixed position in relation to bone fragments while a pin is being driven through the fragments.

Another object of the present invention is to provide a bone transfixion pin guide that is readily adjustable to adapt to the varying diameters and lengths of a variety of bone transfixion pins.

Yet another object of the present invention is to provide a bone transfixion pin guide that can be readily sterilized for multiple usage.

A further object of the present invention is to provide a bone transfixion pin guide that is compact, relatively lightweight and readily manipulated, so as to be readily usable.

A still further object of the present invention is to provide a bone transfixion pin guide that is economically manufactured.

These and other objects and advantages of the present invention will become more apparent from the detailed description of the preferred embodiment, which follows.

BRIEF DESCRIPTION OF THE DRAWING

The detailed description of the preferred embodiment is hereinafter described with reference to the accompanying drawing. The drawing consists of four figures, which are briefly described as follows.

DETAILED DESCRIPTION OF THE PREFERRED EMBODIMENT

Figure 1:
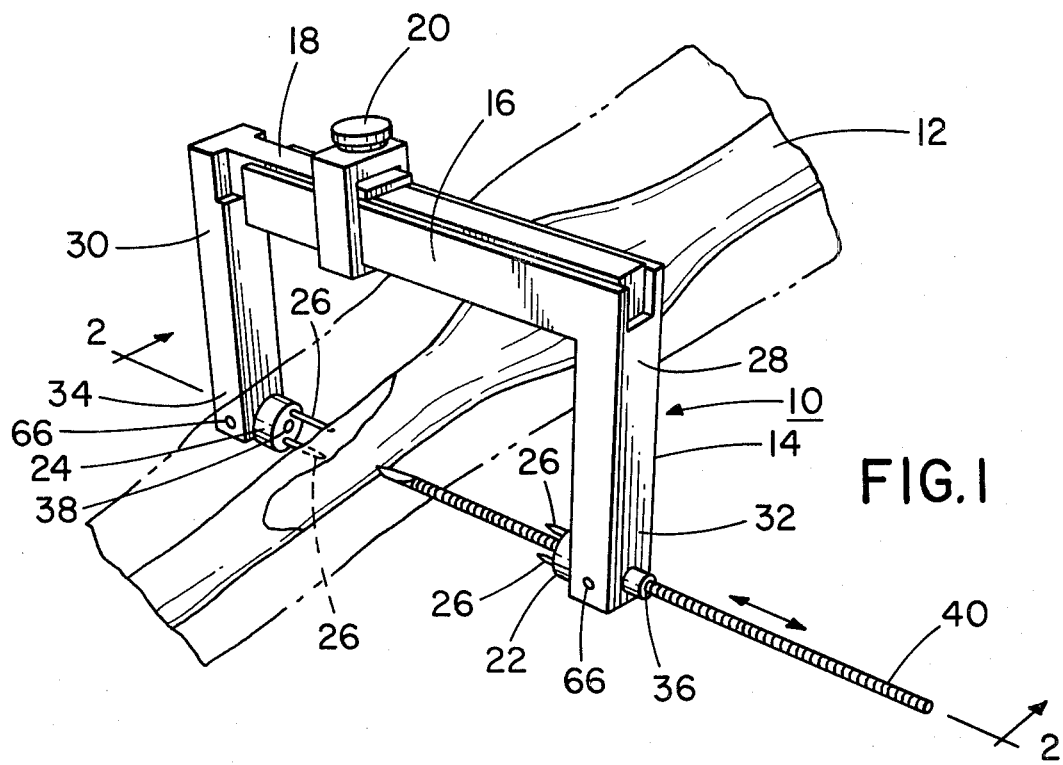
FIG. 1 is a perspective view of the preferred embodiment of the present invention, as typically utilized.

Referring to FIG. 1 of the accompanying drawing, the preferred embodiment of the present invention is shown and generally depicted as a bone transfixion pin guide 10. As depicted, the pin guide is particularly suited for aiding the transfixion of the bone fragments of a fragmented long bone such as bone 12.

Briefly, the pin guide 10, as most preferred, includes a body 14 having a first body portion 16 and a second body portion 18, a lock assembly 20, channel members 22 and 24 and prongs 26. The prongs 26 are embedded in the channel members 22, 24 which are mounted, respectively, on the outer end 32 of the end portions 28 of the body portion 16 and the outer end 34 of the end portion 30 of the body portion 18. The channel members 22, 24 respectively define an entrance channel 36 and an exit channel 38 for a transfixion pin 40. The body portions 16, 18 are moveable in relation to each other, and the lock assembly 20 releasably locks the body portion 16, 18 in a desired relation.

Figure 2:
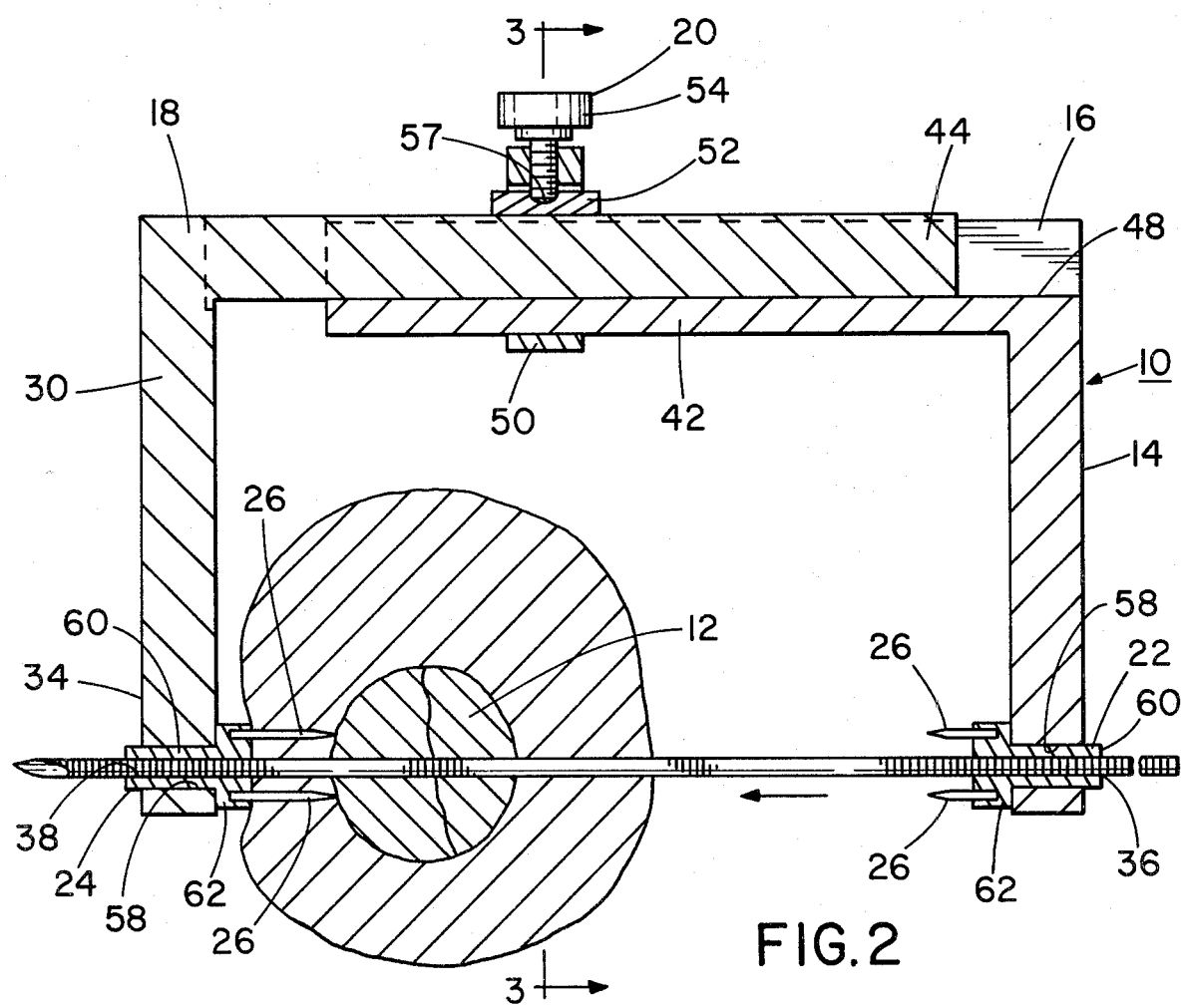
FIG. 2 is a first cross-sectional view of the preferred embodiment, taken along line 2—2 in FIG. 1.
Figure 3:
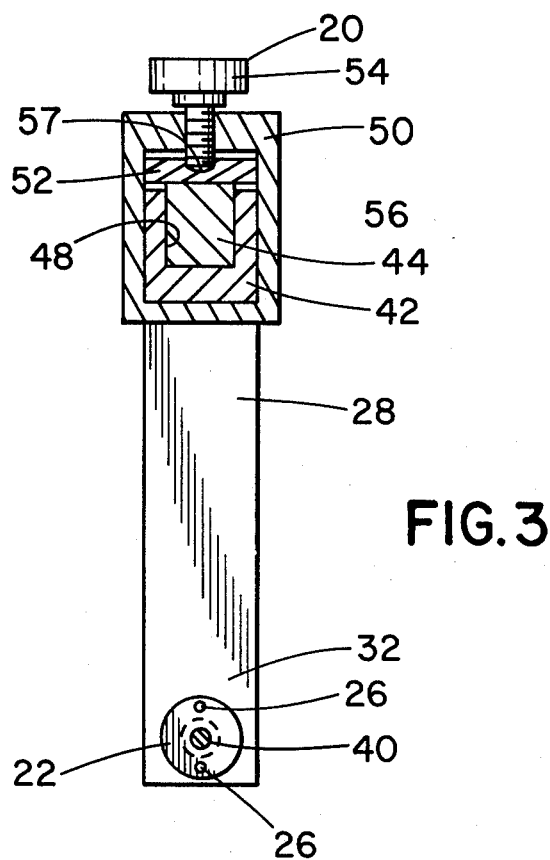
FIG. 3 is a second cross-sectional view of the preferred embodiment, taken along line 3—3 of FIG. 2.

More particularly, and with reference to FIGS. 2 and 3, the first body portion 16 has a central section 42, and the second body portion 18 has a central section 44. For reference, a longitudinal direction is defined parallel to the intended path of the pin 40. As seen in FIG. 2, the longitudinal direction extends horizontally. A transverse direction is also defined, perpendicular to the longitudinal direction. As seen in FIG. 3, the transverse direction lies in the plane of the figure.

With reference to these axes, the central section 44 is rectangular in transverse cross-section and in longitudinal cross-section. The central section 42, in contrast, is U-shaped in transverse cross-section. A rectangular recess 48 is defined in the central section 42. The transverse dimensions of the recess 48 and the central section 44 are matched so that the central section 44 fits loosely within the recess 48. When placed within the recess 48, the central section 44 is thus slideably moveable longitudinally, so that the first body portion 16 and the second body portion 18 are slideably moveable in relation to each other.

As seen best in FIG. 3, the lock assembly 20 includes a rectangular bracket 50, a locking plate 52 and a lock screw 54. The locking bracket 50 is rectangular, defining a rectangular opening 56. With the pin guide 10 assembled, the central sections 42, 44 of the body portions 16, 18 extend through the opening 56. The locking plate 52 is located within the opening 56, atop the central sections 42, 44. The lock screw 54 is threaded through an opening 55 in the bracket 50 and contacts the locking plate 52, within a recess 57 therein. With the lock screw 54 contacting the locking plate 52, the locking plate 52 is captive. By adjusting the lock screw 54 in relation to the bracket 50, the locking plate 52 can be driven so as to lock the central section 44 against the central section 42 and lock the central sections 42, 44 between the locking plate 52 and the bracket 50. The body portions 16, 18 are thus longitudinally moveable in relation to each other, and can be locked in a desired longitudinal relation.

The end sections 28, 30 extend, transversely, perpendicularly from the central sections 42, 44. In transverse direction and transverse length the end sections 28, 30 are substantially identical. At their outer ends 32, 34, each end section 28, 30 defines an opening 58 for the channel members 22, 24. As shown in FIG. 2, the openings 58 are longitudinally and transversely aligned.

Figure 4:
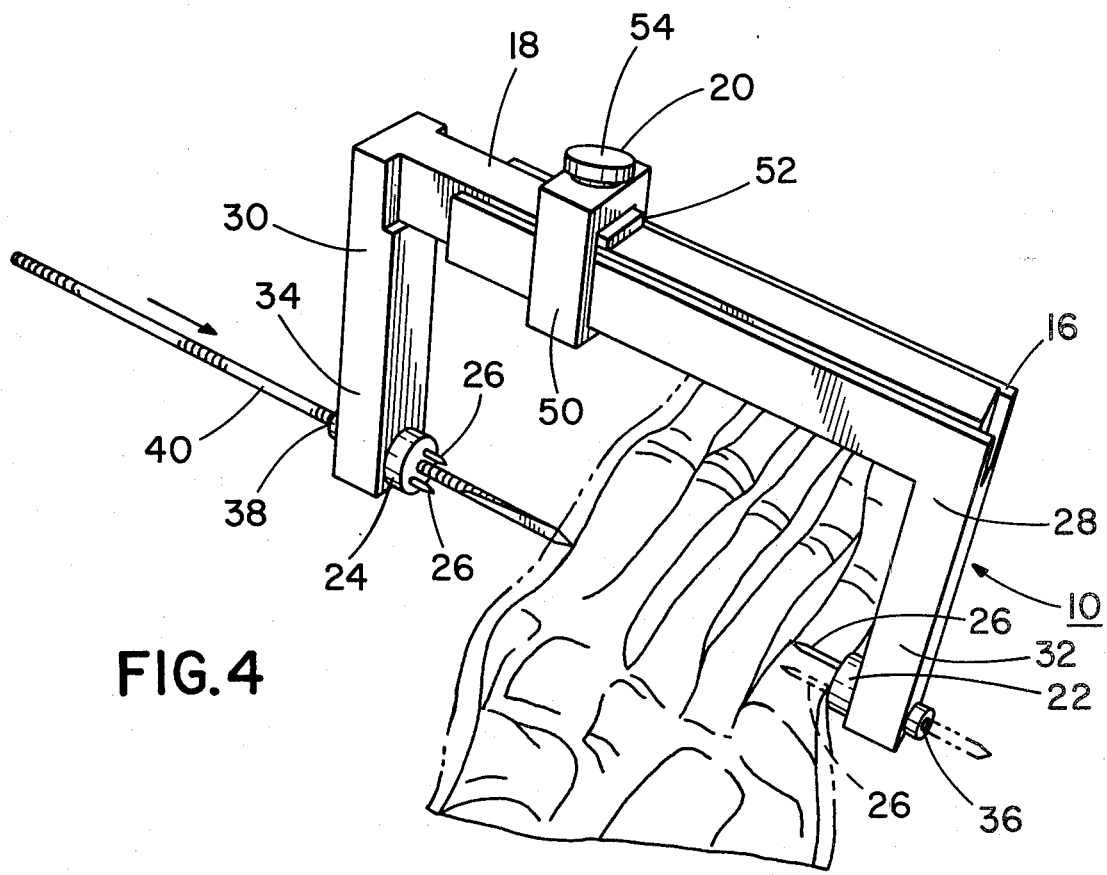
FIG. 4 is a perspective view similar to FIG. 1, depicting the preferred embodiment in a second typical use.

The channel members 22, 24 each include a seat portion 60 and an enlarged head portion 62. Both portions are annular about a central, longitudinally extending channel 36, 38. For convenience, the channel in the channel member 22 is referred to as entrance channel 36, while the channel in the channel member 24 is referred to as exit channel 38. It should be understood that this reference is non-limiting; by comparing FIG. 4 with FIG. 1, it can be seen that the direction of pin travel is a matter of choice.

As seen in FIG. 2, the channels 36, 38 are longitudinally and transversely aligned. In diameter, each channel 36, 38 has a diameter substantially equal to be greater than a diameter of the pin 40. A loose fit with the pin 40 is thus provided.

The channel members 22, 24 face each other. In other words, the head portion 62 of each channel member 22, 24 is oriented toward the other channel member 24, 22. The outer diameter of the head portions 62 is greater than the diameter of the openings 58. Square shoulders are defined between the head portion 62 and the seat portion 60. The channel members 22, 24 thus seat against the inner side of the end portions 28, 30. Transversely directed set screws 66 retain the channel members 22, 24 in position.

The prongs 26 are mounted on the channel members 22, 24. More specifically, two prongs 62 are embedded in the head portion 26 of each channel member 22, 24. The prongs 26 are generally aligned with channels 36, 38, and protrude inward of the inner face of the head portions 62. The two prongs 26 on each head portion 62 are diametrically opposite in relation to the channel 64.

The prongs 26 are for affixing the pin guide 10 in relation to the bone 12. In use, the prongs 26 pierce the fleshy tissues adjacent the insertion site in the bone 12.

The pin guide 10 as now structurally described is utilized as follows. The physician identifies the insertion site by visual observation, examination of X-ray photographs, and the like. Once the insertion site is identified, the physician selects the point of entry for the pin 40 and its point of exit. A pin 40 of appropriate dimensions is then selected, and channel members 22, 24 having appropriately sized channels 36, 38 are placed on the end sections 28, 30 of the pin guide 10. The lock assembly 20 of the pin guide 10 is then loosened and the pin guide 10 placed so that the entrance channel 36 is at the selected entry point and the exit channel 38 is at the selected exit point. The body portions 16, 18 are moved toward each other until the prongs 26 pierce the tissues adjacent the insertion site. The body is then locked and positioned. The selected pin 40 is then placed in a power drill or the like and the tip of the pin 40 is inserted through the entrance channel 36. The pin 40 is then driven through the bone 12, where it exits through the exit channel 38. During the driving of the pin 40, the pin guide 10 is locked in position and the pin 40 is guided by the entrance channel 36. Accurate guidance of the pin 40 thus occurs, and the pin is inserted from the desired entry point to the desired exit point.

A new and useful pin guide 10 has thus been described. As should be apparent, a variety of modifications could be made to the preferred embodiment of the present invention. The preferred embodiment is thus to be considered as illustrative. All modifications which come within the scope and spirit of the appended claims are intended to be embraced therein.

What is claimed is:

1. A bone transfixion pin guide for guiding the insertion of a bone transfixion pin into an insertion site in a bone, comprising:
   a body defining a longitudinal axis and having a first transversely extending end portion and a second transversely extending end portion, said first end portion and said second in portion spaced longitudinally apart from each other and extending generally in the same transverse direction;
   means on said first end portion for defining an entrance channel for said bone transfixion pin;
   means on said second end portion for defining an exit channel for said bone transfixion pin, said exit channel in axial alignment with said entrance channel; and
   means on said first end portion and on said second end portion for affixing the body in relation to the insertion site, said means for affixing the bone transfixion pin guide in relation to the insertion site being means for piercing the fleshy tissue adjacent said insertion site;
   whereby a physician may insert a bone transfixion pin into the bone by affixing the body in relation to the insertion site so that the entrance channel and exit channel lie along the desired path of the bone transfixion pin.

2. A joint transfixion pin guide as in claim 1 in which said means for piercing the fleshy tissue adjacent the insertion site includes prongs.

3. A bone transfixion pin guide as in claim 1 having a body which includes a first body portion and a second body portion, said first body portion and said second body portion cooperatively defining means for moving said first body portion and said second body portion longitudinally in relation to one another, whereby said end portions can be moved longitudinally in relation to one another so as to adapt to bones of various dimensions.

4. A bone transfixion pin guide as in claim 3 wherein said means for moving said first body portion and said second body portion longitduinally in relation to one another is means for slidably moving said first body portion and said second body portion longitudinally in relation to one another.

5. A bone transfixion pin guide as in claim 3 further comprising means mounted on said body for locking said first body portion and said second body portion in a fixed position in relation to one another.

6. A bone transfixion pin guide as in claim 1 wherein said means for defining said entrance channel and said means for defining said exit channel are removable, whereby alternate means for defining a second entrance channel and alternate means for defining a second exit channel can be mounted on said body so that said bone transfixion pin guide can be utilized with bone transfixion pins of more than one diameter.

\* \* \* \* \*